(12) United States Patent
Rollins et al.

(10) Patent No.: US 7,879,749 B2
(45) Date of Patent: Feb. 1, 2011

(54) METHODS OF USING STRUCTURES INCLUDING CATALYTIC MATERIALS DISPOSED WITHIN POROUS ZEOLITE MATERIALS TO SYNTHESIZE HYDROCARBONS

(75) Inventors: Harry W. Rollins, Idaho Falls, ID (US); Lucia M. Petkovic, Idaho Falls, ID (US); Daniel M. Ginosar, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 480 days.

(21) Appl. No.: 11/464,566

(22) Filed: Aug. 15, 2006

(65) Prior Publication Data

US 2008/0045403 A1    Feb. 21, 2008

(51) Int. Cl.
*B01J 29/04*    (2006.01)
*C01B 39/00*    (2006.01)

(52) U.S. Cl. .............. 502/62; 502/64; 502/71; 502/77; 502/78; 502/79; 518/713; 518/714; 518/715; 518/721; 585/639; 585/640

(58) Field of Classification Search ......... 585/639–640; 518/713, 714, 715, 721; 502/62, 64, 71, 502/77, 78, 79
See application file for complete search history.

(56) References Cited

U.S. PATENT DOCUMENTS

| | | | |
|---|---|---|---|
| 3,615,217 A | 10/1971 | O'Brien et al. | |
| 3,702,886 A | 11/1972 | Argauer et al. | |
| 3,907,715 A | 9/1975 | Arai et al. | |
| 4,863,894 A | 9/1989 | Chinchen et al. | |
| 5,043,307 A | 8/1991 | Bowes et al. | |
| 5,137,924 A * | 8/1992 | Short et al. | 518/700 |
| 5,344,849 A * | 9/1994 | Ayasse | 518/713 |
| 5,348,643 A | 9/1994 | Absil et al. | |
| 5,348,924 A | 9/1994 | Potter et al. | |
| 5,366,948 A | 11/1994 | Absil et al. | |
| 5,378,440 A | 1/1995 | Herbst et al. | |
| 5,456,821 A | 10/1995 | Absil et al. | |
| 5,466,646 A | 11/1995 | Moser | |

(Continued)

OTHER PUBLICATIONS

Baerlocher et al., "Atlas of Zeolite Framework Types," 5th Rev. ed., Elsevier, pp. 1-19 (with attached Framework Type Data Sheets) (2001).

(Continued)

*Primary Examiner*—Prem C Singh
(74) *Attorney, Agent, or Firm*—TraskBritt

(57) ABSTRACT

Catalytic structures include a catalytic material disposed within a zeolite material. The catalytic material may be capable of catalyzing a formation of methanol from carbon monoxide and/or carbon dioxide, and the zeolite material may be capable of catalyzing a formation of hydrocarbon molecules from methanol. The catalytic material may include copper and zinc oxide. The zeolite material may include a first plurality of pores substantially defined by a crystal structure of the zeolite material and a second plurality of pores dispersed throughout the zeolite material. Systems for synthesizing hydrocarbon molecules also include catalytic structures. Methods for synthesizing hydrocarbon molecules include contacting hydrogen and at least one of carbon monoxide and carbon dioxide with such catalytic structures. Catalytic structures are fabricated by forming a zeolite material at least partially around a template structure, removing the template structure, and introducing a catalytic material into the zeolite material.

16 Claims, 5 Drawing Sheets

U.S. PATENT DOCUMENTS

| | | | |
|---|---|---|---|
| 5,506,273 | A | 4/1996 | Haruta et al. |
| 5,536,894 | A | 7/1996 | Degnan et al. |
| 5,689,024 | A | 11/1997 | Schmitt |
| 5,695,735 | A | 12/1997 | Benazzi et al. |
| 5,786,294 | A | 7/1998 | Sachtler et al. |
| 5,919,430 | A | 7/1999 | Hasenzahl et al. |
| 5,955,049 | A | 9/1999 | Ogata et al. |
| 6,121,187 | A | 9/2000 | Maier |
| 6,297,180 | B1 | 10/2001 | Maier |
| 6,403,743 | B1 | 6/2002 | Clark et al. |
| 6,497,812 | B1 | 12/2002 | Schinski |
| 6,620,402 | B2 | 9/2003 | Jacobsen et al. |
| 6,620,983 | B1 | 9/2003 | Cao et al. |
| 6,627,572 | B1 | 9/2003 | Cai et al. |
| 6,638,892 | B1 | 10/2003 | Wu et al. |
| 6,680,278 | B2 | 1/2004 | Cao et al. |
| 6,686,511 | B2 | 2/2004 | Miller et al. |
| 6,706,936 | B2 | 3/2004 | O'Rear et al. |
| 6,812,373 | B2 | 11/2004 | Wang |
| 6,841,711 | B2 | 1/2005 | Krug et al. |
| 6,914,030 | B2 | 7/2005 | Cao et al. |
| 6,936,566 | B2 | 8/2005 | Mees et al. |
| 6,982,287 | B2 | 1/2006 | Wang et al. |
| 6,989,470 | B2 | 1/2006 | Wang |
| 7,005,118 | B2 | 2/2006 | Rojas et al. |
| 7,022,888 | B2 | 4/2006 | Choudhary et al. |
| 7,048,781 | B1 | 5/2006 | Lovell |
| 7,064,097 | B1 | 6/2006 | Cai et al. |
| 2004/0064008 | A1* | 4/2004 | Maurer et al. ............... 585/640 |
| 2004/0234823 | A1 | 11/2004 | Burgener, II et al. |

OTHER PUBLICATIONS

Bessell, Sandra, "Support effects in cobalt-based Fisher-Tropsch catalysis," Applied Catalysis A: General 96: 253-268 (1993).

Cundy et al., "The Hydrothermal Synthesis of Zeolites: History and Development from the Earliest Days to the Present Time," Chem. Rev. 103: 663-701 (2003).

"Fischer-Tropsch process," Wikipedia, <<hhtp://en.wikipedia.org/wiki/Fischer-Tropsch>> 3 pages (2006).

Fornasari et al., "Cobalt-Modified Cu-Zn-Cr Catalysts in the Synthesis of Methanol," Journal of Catalysis, 135: 386-399 (1992).

Fukuoka et al., "Ship-in-bottle synthesis and catalytic performances of platinum carbonyl clusters, nanowires, and nanoparticles in micro- and mesoporous materials," Catalysis Today 66: 23-31 (2001).

Fujitani et al., "Methanol Synthesis from CO and $CO_2$ Hydrogenations over Supported Palladium Catalysts," Bull. Chem. Soc. Jpn., 75: 1393-1398 (2002).

Fujiwara et al., "Change of catalytic properties of Fe-ZnO/zeolite composite catalyst in the hydrogenation of carbon dioxide," Applied Catalysis A: General 154: 87-101 (1997).

Fujiwara, et al., "Hydrogenation of carbon dioxide over copper-pyrochlore/zeolite composite catalysts," Catalysis Today 29: 343-348 (1996).

Hadjigeorghiou et al., "Fischer-Tropsch Activity in $NiO-ThO_2$ Catalysts," Applied Catalysis, 21: 47-59 (1986).

Hartmann et al., "Transition-Metal Ions in Aluminophosphate and Silicoaluminophosphate Molecular Sieves: Location, Interaction with Adsorbates and Catalytic Properties," Chemical Reviews, vol. 99, No. 3 (1999).

Iwasa et al., "Methanol synthesis from $CO_2$ under atmospheric pressure over supported Pd catalysts," Catalysis Letters, vol. 96, Nos. 1-2: 75-78 (2004).

Klier, K., "Structure and Function of Real Catalysts," Applications of Surface Science, 19: 267-297 (1984).

Komatsu et al., "Fischer-Tropsch synthesis on RuTi intermetallic compound catalyst," Applied Catalysis A: General 279: 173-180 (2005).

Li et al., "Direct synthesis of middle *iso*-paraffins from synthesis gas," Catalysis Today 84: 59-65 (2003).

Li et al., "Direct synthesis of middle iso-paraffins from synthesis gas on hybrid catalysts," Catalysis Today 89: 439-446 (2004).

Liaw et al., "Liquid-phase synthesis of methanol from $CO_2/H_2$ over ultrafine CuB catalysts," Applied Catalysis A: General 206: 245-256 (2001).

Liu et al., "Surface active structure of ultra-fine $Cu/ZrO_2$ catalysts used for the $CO_2+H_2$ to methanol reaction," Applied Catalysis A: General 218: 113-119 (2001).

Liu et al., "Recent Advances in Catalysts for Methanol Synthesis via Hydrogenation of CO and $CO_2$," Ind. Eng. Chem. Res. 42: 6518-6530 (2003).

Lok et al., "Silicoaluminophosphate Molecular Sieves: Another New Class of Microporous Crystalline Inorganic Solids," J. Am. Chem. Soc., 106: 6092-6093 (1984).

Maitlis et al., "Towards a chemical understanding of the Fischer-Tropsch reaction: alkene formation," Applied Catalysis A: General 186: 363-374 (1999).

Meier, W.M., "Zeolites and zeolite-like materials," Pure & Appl. Chem., vol. 58, No. 10, pp. 1323-1328 (1986).

Melián-Cabrera et al., "Pd-Modified Cu-Zn Catalysts for Methanol Synthesis from $CO_2/H_2$ Mixtures: Catalytic Structures and Performance," Journal of Catalysis 210: 285-294 (2002).

"Methanol and Methanol Derivative," pp. 29-47 (before Aug. 2, 2006).

Nakatsuji et al., "Mechanism of Methanol Synthesis on Cu(100) and Zn/Cu(100) Surfaces: Comparative Dipped Adcluster Model Study," International Journal of Quantum chemistry, vol. 77, 341-349 (2000).

Nam et al., "Catalytic conversion of carbon dioxide into hydrocarbons over iron supported on alkali ion-exchanged Y-zeolite catalysts," Applied Catalysis A: General 179: 155-163 (1999).

Park et al., "Catalytic Reduction of Carbon Dioxide," Energy Convers. Mgmt., vol. 36, No. 6-9, pp. 573-576 (1995).

Patterson et al., "Carbon monoxide hydrogenation over molybdenum and tungsten carbides," Applied Catalysis A: General 251: 449-455 (2003).

"The Production of Methanol and Gasoline," VII-Energy-D-Methanol, pp. 1-19 (before Aug. 2, 2006).

Riedel et al., "Comparative study of Fischer-Tropsch synthesis with $H_2/CO$ and $H_2/CO_2$ syngas using Fe- and Co-based catalysts," Applied Catalysis A: General 186: 201-213 (1999).

Saito et al., "Development of Cu/ZnO-Based High Performance Catalysts for Methanol Synthesis by $CO_2$ Hydrogenation," Energy Convers. Mgmt. vol. 36, No. 6-9, pp. 577-580 (1995).

Schmidt et al., "Carbon Nanotube Templated Growth of Mesoporous Zeolite Single Crystals," Chem. Mater. 13: 4416-4418 (2001).

Shannon et al., "Characterization of Catalytic Surfaces by Isotopic-Transient Kinetics during Steady-State Reaction," Chem. Rev. 95: 677-695 (1995).

Song et al., "Direct synthesis of isoalkanes through Fischer-Tropsch reaction on hybrid catalysts," Applied Catalysis A: General 110: 121-136 (1994).

Stöcker, Michael, "Methanol-to-hydrocarbons: catalytic materials and their behavior," Microporous and Mesoporous Materials, 29: 3-48 (1999).

Toyir et al., "Catalytic performance for $CO_2$ conversion to methanol of gallium-promoted copper-based catalysts: influence of metallic precursors," Applied Catalysis B: Environmental 34: 255-266 (2001).

Tsubaki et al., "Three-component hybrid catalyst for direct synthesis of isoparaffin via modified Fischer-Tropsch synthesis," Catalysis Communications 4: 108-111 (2003).

Xu et al., "The promotions of MnO and $K_2O$ to Fe/silicalite-2 catalyst for the production of light alkenes from $CO_2$ hydrogenation," Applied Catalysis A: General 173: 19-25 (1998).

Xu et al., "Hydrogenation of carbon dioxide over Fe-Cu-Na/zeolite composite catalysts: Na migration via solid-solid reaction and its effects on the catalytic activity," Journal of Molecular Catalysis A: Chemical 136: 161-168 (1998).

Xu et al., "Improved activity of Fe-Cu catalysts by physical mixing with zeolites for the hydrogenation of carbon dioxide," Journal of Molecular Catalysis A: Chemical 120: L23-L26 (1997).

Yao et al., "Ultrasound as a tool to synthesize nano-sized silica-alumina catalysts with controlled mesoporous distribution by a novel sol-gel process," Catalysis Letters, vol. 78, Nos. 1-4: 37-41 (2002).

Yin et al., "Mesoporous HMS molecular sieves supported cobalt catalysts for Fischer-Tropsch synthesis," Microporous and Mesoporous Materials 47: 15-24 (2001).

Zhang et al., "CO and $CO_2$ hydrogenation study on supported cobalt Fischer-Tropsch synthesis catalysts," Catalysis Today 71: 411-418 (2002).

Agny et al., "Synthesis of Methanol from Carbon Monoxide and Hydrogen Over a Copper-ZincOxide-Alumina Catalyst," Ind. Eng. Chem. Prod.Res.Dev. (1985) 24:50-55.

Govind et al., "Zeolite-Catalyzed Hydrocarbon Formation From Methanol: Denisty Functional Simulations," Int. J. Mol. Sci. (2002) 3:423-434.

Kniep et al., "Rational Design of Nanostructured Copper-Zinc Oxide Catalysts for the Steam Reforming of Methanol," Angew. Chem. Int. Ed. 2004, 43, 112-115.

Kresge et al., "Ordered Mesoporous Molecular Sieves Synthesized by a Liquid-Crystal Template Mechanism," Nature (1992) 359:710-712.

Ponec, V., "Active Centres for Synthesis Gas Reactions,"Catalysis Today, 12 (1992) 227-254.

Tang et al., "Mono-sized single-Walled Nanotubes Formed in Channels of ALPO4-5 Single Crystal," Applied Physics Letters, Oct. 19, 1998, 73:2287-2289.

* cited by examiner

METHODS OF USING STRUCTURES INCLUDING CATALYTIC MATERIALS DISPOSED WITHIN POROUS ZEOLITE MATERIALS TO SYNTHESIZE HYDROCARBONS

GOVERNMENT RIGHTS

This invention was made with government support under Contract No. DE-AC07-05ID14517 awarded by the United States Department of Energy. The government has certain rights in the invention.

CROSS-REFERENCE TO RELATED APPLICATION

This application is related to U.S. patent application Ser. No. 11/688,930, filed Mar. 21, 2007, now U.S. Pat. No. 7,592,291, issued Sep. 22, 2009, which is a continuation-in-part of this application.

FIELD OF THE INVENTION

The present invention relates to catalytic materials, structures, systems, and methods. More particularly, the present invention relates to catalytic structures including zeolite materials, and to systems and methods for synthesizing hydrocarbon molecules from hydrogen and at least one of carbon monoxide and carbon dioxide using such catalytic structures. The present invention also relates to methods of fabricating catalytic structures that include zeolite materials.

BACKGROUND OF THE INVENTION

Carbon dioxide gas ($CO_2$) may be converted into liquid fuels such as, for example, hydrocarbon molecules of between about 5 and about 12 carbon atoms per molecule (e.g., gasoline) through multi-step reactions. For example, carbon dioxide ($CO_2$) gas and hydrogen ($H_2$) may be converted to carbon monoxide (CO) gas and water ($H_2O$) through the Reverse Water-Gas Shift Reaction, which is shown by Reaction [1] below.

$$CO_2 + H_2 \rightarrow CO + H_2O \qquad [1]$$

Synthesis gas, which is a mixture of carbon monoxide gas (CO) and hydrogen gas ($H_2$) then may be produced from the reaction products of the Reverse Water-Gas Shift Reaction by adding additional hydrogen gas ($H_2$) to the reaction products. This synthesis gas may be further reacted through either Fischer-Tropsch (FT) processes, or through methanol synthesis (MS) plus methanol-to-gasoline (MTG) processes, to provide liquid fuels.

Briefly, Fischer-Tropsch processes include various catalyzed chemical reactions in which synthesis gas is converted into liquid hydrocarbons in a reactor in the presence of a catalyst and at temperatures between about 200° C. and about 350° C. Catalysts used in Fischer-Tropsch processes include, for example, iron, cobalt, nickel, and ruthenium. While various interrelated reactions may occur in Fischer-Tropsch processes, the overall reaction process may be generally represented by Reaction [2] below.

$$(2n+1)H_2 + nCO \rightarrow C_nH_{2n+2} + nH_2O \qquad [2]$$

As mentioned above, synthesis gas may also be reacted by first performing a methanol synthesis (MS) process, and then performing a methanol-to-gasoline (MTG) process to produce liquid fuels. Methanol synthesis (MS) processes involve the catalytic conversion of carbon monoxide, carbon dioxide, hydrogen, and water to methanol and other reaction byproducts. The methanol synthesis reactions may be generally represented by Reactions [3], [4], and [5] below.

$$CO + 2H_2 \rightarrow CH_3OH \qquad [3]$$

$$CO_2 + 3H_2 \rightarrow CH_3OH + H_2O \qquad [4]$$

$$CO + H_2O \rightarrow CO_2 + H_2 \qquad [5]$$

The methanol-to-gas (MTG) process involves the conversion of methanol to hydrocarbon molecules using zeolite catalysts, which are described in further detail below. The methanol-to-gas (MTG) process occurs in two steps. First, methanol is heated to about 300° C. and partially dehydrated over an alumina catalyst at about 2.7 megapascals to yield an equilibrium mixture of methanol, dimethyl ether, and water. This effluent is then mixed with synthesis gas and introduced into a reactor containing a zeolite catalyst (such as, for example, a ZSM-5 zeolite), at temperatures between about 350° C. and about 366° C. and at pressures between about 1.9 megapascals and about 2.3 megapascals, to produce hydrocarbons and water. The methanol-to-gas (MTG) reactions may be generally represented by Reactions [6], [7], and [8] below.

$$2CH_3OH \rightarrow CH_3OCH_3 + H_2O \qquad [6]$$

$$CH_3OCH_3 \rightarrow C_2\text{-}C_5 \text{ Olefins} \qquad [7]$$

$$C_2\text{-}C_5 \text{ Olefins} \rightarrow \text{Paraffins, Cycloparaffins, Aromatics} \qquad [8]$$

While the feasibility of the above-described reactions has been demonstrated, mass production of liquid fuels using such processes has not been widely implemented due, at least in part, to the relatively high costs associated with carrying out the reactions, and to the relatively low yields exhibited by the reactions.

In an effort to improve the yield of the various reactions and to minimize the costs associated with carrying out the reactions, research has been conducted in an effort to improve the efficiency of the catalysts associated with each of the respective catalyzed reactions. As previously mentioned, zeolites have been used as catalysts in the methanol-to-gas (MTG) process.

Zeolites are substantially crystalline oxide materials in which the crystal structure of the oxide material defines pores, channels, or both pores and channels in the oxide material. Such pores and channels may have cross-sectional dimensions of between about 1 angstrom and about 200 angstroms, and typically have cross-sectional dimensions of between about 3 angstroms and about 15 angstroms. Typically, zeolite materials include metal atoms (classically, silicon or aluminum) that are surrounded by four oxygen anions to form an approximate tetrahedron consisting of a metal cation at the center of the tetrahedron and oxygen anions at the four apexes of the tetrahedron. The tetrahedral metals are often referred to as "T-atoms." These tetrahedra then stack in substantially regular arrays to form channels. There are various ways in which the tetrahedra may be stacked, and the resulting "frameworks" have been documented and categorized in, for example, Ch. Baerlocher, W. M. Meier and D. H. Olson, *Atlas of Zeolite Framework Types*, 5th ed., Elsevier: Amsterdam, 2001, the contents of which are hereby incorporated herein in their entirety by this reference.

Silicon-based tetrahedra in zeolitic materials are electrically neutral since silicon typically exhibits a 4+ oxidation state. Tetrahedra based on elements other than silicon, however, may not be electrically neutral, and charge-compensating ions may be present so as to electrically neutralize the non-neutral tetrahedra. For example, many zeolites are aluminosilicates. Aluminum typically exists in the 3+ oxidation state, and charge-compensating cations typically populate the pores to maintain electrical neutrality. These charge-compensating cations may participate in ion-exchange processes. When the charge-compensating cations are protons, the zeolite may be a relatively strong solid acid. The acidic properties of such solid acid zeolites may contribute to their catalytic properties. Other types of reactive metal cations may also populate the pores to form catalytic materials with unique properties.

Notwithstanding the research that has been conducted with respect to the above-described reactions and their respective catalytic materials, there remains a need in the art for catalytic materials and structures than can be used to provide a direct route or mechanism for the reduction of carbon monoxide (CO) and/or carbon dioxide ($CO_2$) to liquid fuels.

BRIEF SUMMARY OF THE INVENTION

In one example embodiment, the present invention includes a catalytic structure that includes a substantially crystalline zeolite material having a first plurality of pores and a second plurality of pores. The pores of the first plurality are substantially defined by interstitial spaces within the crystal structure of the substantially crystalline zeolite material. The pores of the second plurality are dispersed throughout the substantially crystalline zeolite material. A metallic material may be disposed within at least one pore of at least one of the first plurality of pores and the second plurality of pores. A metal oxide material also may be disposed within at least one pore of at least one of the first plurality of pores and the second plurality of pores.

In another example embodiment, the present invention includes a catalytic structure that includes a zeolite material that is capable of catalyzing the formation of hydrocarbon molecules having two or more carbon atoms from methanol, and at least one catalytic material that is capable of catalyzing the formation of methanol from at least one of carbon monoxide and carbon dioxide in the presence of hydrogen disposed within the zeolite material. The zeolite material includes a first plurality of pores substantially defined by interstitial spaces within the crystal structure of the zeolite material, and a second plurality of pores dispersed throughout the zeolite material. The catalytic material may be disposed within at least one pore of at least one of the first plurality of pores and the second plurality of pores.

In an additional example embodiment, the present invention includes methods of fabricating catalytic structures. A zeolite material capable of catalyzing the formation of hydrocarbon molecules from methanol may be formed at least partially around at least one template structure. The template structure may be removed from within the zeolite material, and at least one catalytic material capable of catalyzing the formation of methanol from at least one of carbon monoxide and carbon dioxide in the presence of hydrogen is introduced into the zeolite material.

In yet a further example embodiment, the present invention includes methods of synthesizing hydrocarbon molecules having two or more carbon atoms in which hydrogen and at least one of carbon monoxide and carbon dioxide are contacted with a catalytic structure. The catalytic structure includes a zeolite material that is capable of catalyzing the formation of hydrocarbon molecules having two or more carbon atoms from methanol, and at least one catalytic material that is capable of catalyzing the formation of methanol from at least one of carbon monoxide and carbon dioxide in the presence of hydrogen disposed within the zeolite material. The zeolite material includes a first plurality of pores substantially defined by interstitial spaces within the crystal structure of the zeolite material, and a second plurality of pores dispersed throughout the zeolite material. The catalytic material may be disposed within at least one pore of at least one of the first plurality of pores and the second plurality of pores.

In still another example embodiment, the present invention includes systems for synthesizing hydrocarbon molecules from hydrogen and at least one of carbon monoxide and carbon dioxide. The systems include a catalytic structure disposed within a reactor. The catalytic structure includes a zeolite material that is capable of catalyzing the formation of hydrocarbon molecules having two or more carbon atoms from methanol, and at least one catalytic material that is capable of catalyzing the formation of methanol from at least one of carbon monoxide and carbon dioxide in the presence of hydrogen disposed within the zeolite material. The zeolite material includes a first plurality of pores substantially defined by interstitial spaces within the crystal structure of the zeolite material, and a second plurality of pores dispersed throughout the zeolite material. The catalytic material may be disposed within at least one pore of at least one of the first plurality of pores and the second plurality of pores.

BRIEF DESCRIPTION OF THE SEVERAL VIEWS OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Figure 1:
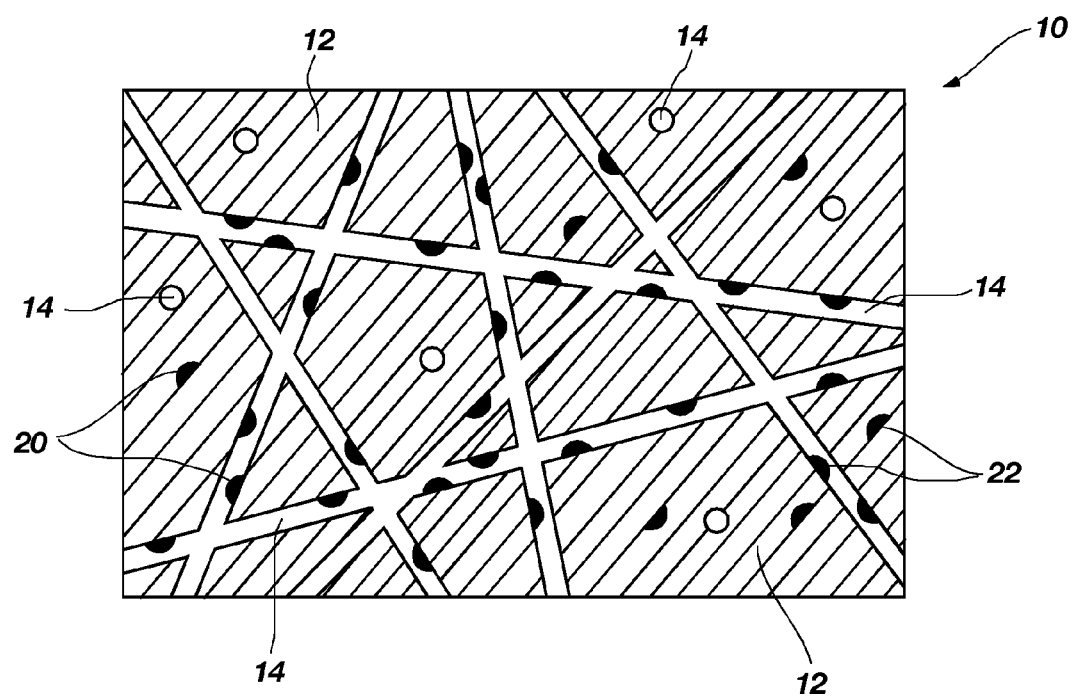
FIG. 1 is a cross-sectional view of one example of a catalytic structure that embodies teachings of the present invention and includes a metal material and a metal oxide material that are disposed within pores of a zeolite material.

As used herein, the term "zeolite material" means and includes any substantially crystalline material generally represented by the formula:

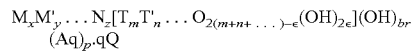

wherein M and M' represent exchangeable and/or non-exchangeable metal cations, N represents non-metallic cations (which may be removable upon heating), T and T' represent T atoms (which may be selected from, for example, beryllium, boron, aluminum, silicon, phosphorous, gallium, and germanium), O represents oxygen atoms, OH represents hydroxide ions, Aq represents chemically bonded water (or any other strongly held ligands of the T-atoms (e.g., T and T'), and Q represents sorbate molecules, which may be, but are not limited to, water molecules. In the above formula, x, y, z, m, n, $\epsilon$, br, p, and q each may be any number greater than or equal to zero. In other words, if one of the components is not present in the material, then the corresponding subscript would be zero. The portion of the formula contained within the brackets provides the framework of the substantially crystalline material. The crystal structure of zeolite materials typically includes a plurality of interconnected tetrahedra and has a framework density (FD) of between about 12 and about 23, wherein the framework density is defined as the number of tetrahedrally coordinated atoms (T-atoms) per 1,000 cubic angstroms. By way of example and not limitation, zeolite materials include aluminosilicate based materials, aluminophosphate-based materials, and silicoaluminophosphate-based materials. An example of a zeolite material is an aluminosilicate-based material having a chemical structure in which the unit cell (smallest geometrically repeating unit of the crystal structure) is generally represented by the formula:

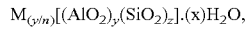

$$M_{(y/n)}[(AlO_2)_y(SiO_2)_z] \cdot (x)H_2O,$$

wherein M is a cation selected from elements in Group IA and Group IIA of the Periodic Table of the Elements (including, for example, sodium, potassium, magnesium and calcium), n is the valence of the cations M, x is the number of water molecules per unit cell, y is the number of $AlO_2$ units per unit cell, and z is the number of $SiO_2$ units per unit cell. In some zeolite materials, the ratio of z to y (z/y) may be any number greater than 1. Another example of a zeolite material is a silicoaluminophosphate-based material having a chemical structure in which the unit cell is generally represented by the formula:

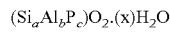

$$(Si_aAl_bP_c)O_2 \cdot (x)H_2O$$

wherein x is the number of water molecules per unit cell, z is the number of silicon atoms per unit cell, b is the number of aluminum atoms per unit cell, and c is the number of phosphorous atoms per unit cell. Such silicoaluminophosphate-based materials may also include a small amount of organic amine or quaternary ammonium templates, which are used to form the materials and retained therein. Such zeolite materials may further include additional elements and materials disposed within the interstitial spaces of the unit cell.

As used herein, the term "pore" means and includes any void in a material and includes voids of any size and shape. For example, pores include generally spherical voids, generally rectangular voids, as well as elongated voids or channels having any cross-sectional shape including nonlinear or irregular shapes.

As used herein, the term "micropore" means and includes any void in a material having an average cross-sectional dimension of less than about 20 angstroms (2 nanometers). For example, micropores include generally spherical pores having average diameters of less than about 20 angstroms, as well as elongated channels having average cross-sectional dimensions of less than about 20 angstroms.

As used herein, the term "mesopore" means and includes any void in a material having an average cross-sectional dimension of greater than about 20 angstroms (2 nanometers) and less than about 500 angstroms (50 nanometers). For example, mesopores include generally spherical pores having average diameters between about 20 angstroms and about 500 angstroms, as well as elongated channels having average cross-sectional dimensions between about 20 angstroms and about 500 angstroms.

As used herein, the term "macropore" means and includes any void in a material having an average cross-sectional dimension of greater than about 500 angstroms (50 nanometers). For example, macropores include generally spherical pores having average diameters greater than about 500 angstroms, as well as elongated channels having average cross-sectional dimensions greater than about 500 angstroms.

The illustrations presented herein are not meant to be actual views of any particular catalytic structure, reactor, or system, but are merely idealized representations, which are employed to describe the present invention. Additionally, elements common between figures may retain the same numerical designation.

One example of a catalytic structure 10 that embodies teachings of the present invention is shown in FIG. 1. The catalytic structure 10 includes a zeolite material 12 that is capable of catalyzing the formation of hydrocarbon molecules having two or more hydrocarbons from methanol. As discussed in further detail below, the zeolite material 12 may have both a mesoporous structure and a microporous structure.

Referring to FIG. 1, the catalytic structure 10 may include a plurality of mesopores 14 dispersed throughout the zeolite material 12. The mesopores 14 may include elongated channels extending randomly through the zeolite material 12. By way of example and not limitation, some of the mesopores 14 may include an elongated pore having a generally cylindrical shape and an average cross-sectional diameter in a range extending from about 20 angstroms (2 nanometers) to about 500 angstroms (50 nanometers). Other mesopores 14 may be generally spherical and may have an average diameter in a range extending from about 20 angstroms (2 nanometers) to about 500 angstroms (50 nanometers). In additional embodiments, the mesopores 14 may be disposed in an ordered array within the zeolite material 12. For example, the mesopores 14 may include elongated channels extending generally parallel to one another through the zeolite material 12. In some embodiments, communication may be established between at least some of the mesopores 14. In additional embodiments, each mesopore 14 may be substantially isolated from other mesopores 14 by the zeolite material 12. Furthermore, the zeolite material 12 may include a plurality of macropores in addition to, or in place of, the plurality of mesopores 14.

In one embodiment of the present invention, the zeolite material 12 may have an MFI framework type as defined in Ch. Baerlocher, W. M. Meier and D. H. Olson, *Atlas of Zeolite Framework Types*, 5th ed., Elsevier: Amsterdam, 2001. Furthermore, the zeolite material 12 may include an aluminosilicate-based material. By way of example and not limitation, the zeolite material 12 may include ZSM-5 zeolite material, which is an aluminosilicate-based zeolite material having an MFI framework type. Furthermore, the zeolite material 12 may be acidic. For example, at least some metal cations of the zeolite material 12 may be replaced with hydrogen ions to provide a desired level of acidity to the zeolite material 12. Ion exchange reactions for replacing metal cations in a zeolite material with hydrogen ions are known in the art.

Figure 2:
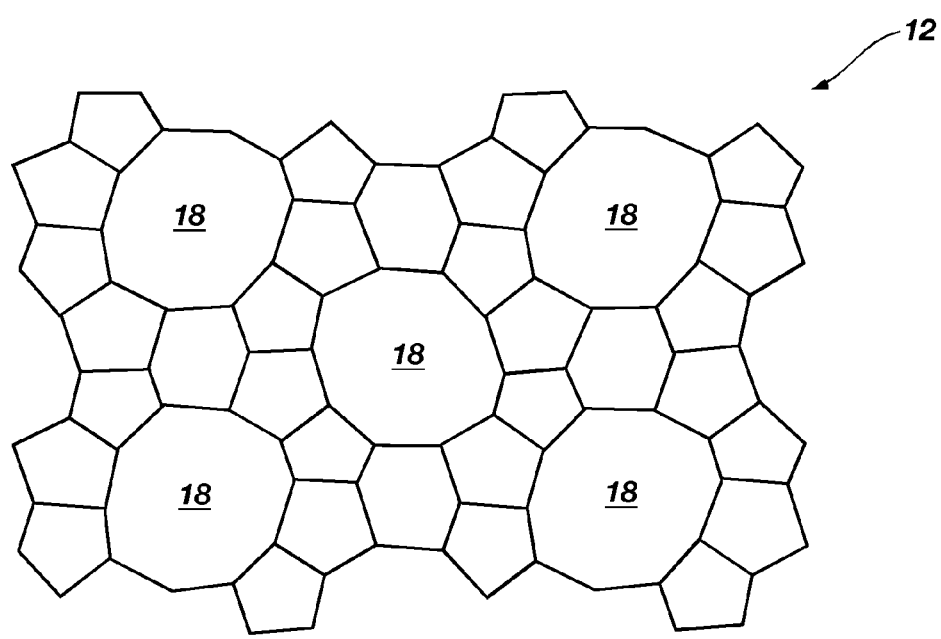
FIG. 2 is a simplified illustration representing one example of a chemical structure framework that may be exhibited by the zeolite material shown in FIG. 1.

FIG. 2 is an enlarged view of a portion of the zeolite material 12 shown in FIG. 1 and provides a simplified representation of the chemical structure framework of a zeolite material 12 having an MFI framework type, as viewed in the [010] direction. As shown therein, the zeolite material 12 may include a plurality of micropores 18 that extend through the zeolite material 12 and are substantially defined by the interstitial spaces within the crystal structure of the zeolite material 12. The micropores 18, shown in FIG. 2, may be substantially straight. The zeolite material 12 may further include additional micropores (not shown in FIG. 2) that extend through the zeolite material 12 in the [100] direction in a generally sinusoidal pattern.

Various types of zeolite materials 12 are known in the art, and any zeolite material 12 that exhibits catalytic activity with respect to the formation of hydrocarbon molecules from methanol, as discussed in further detail below, may be used in catalytic structures that embody teachings of the present invention, such as the catalytic structure 10 shown in FIG. 1. For example, the zeolite material 12 may include a silicoaluminophosphate-based material. Furthermore, the zeolite material 12 may have framework types other than MFI. By way of example and not limitation, the zeolite material 12 may have a BEA, FAU, MOR, FER, ERI, OFF, CHA or an AEI framework type. By way of example and not limitation, the zeolite material 12 may include SAPO-34 (CHA) or ALPO$_4$-18 (AEI).

Figure 3:
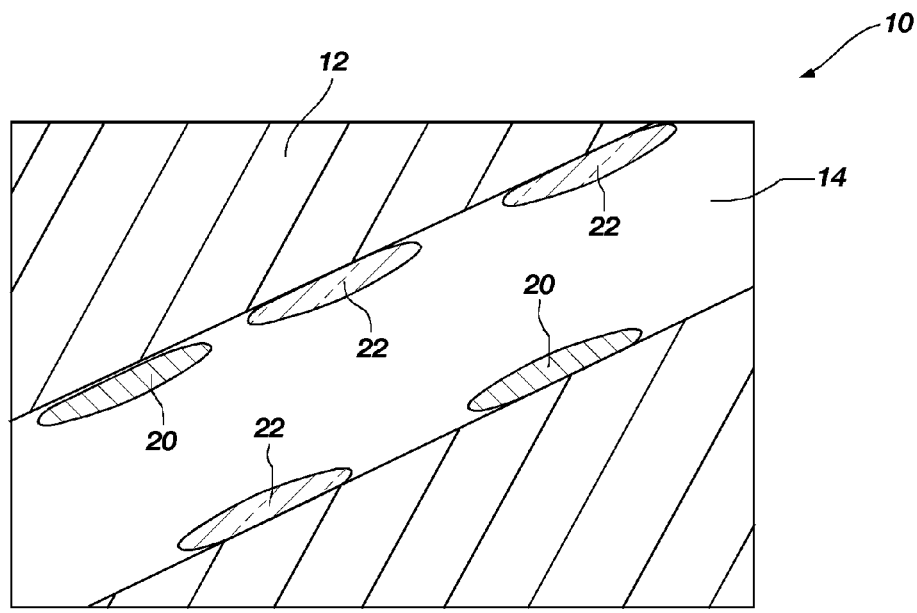
FIG. 3 is an enlarged cross-sectional view of a pore extending through the zeolite material shown in FIG. 1 and illustrating catalytic material within the pore.

Referring to FIG. 3, the catalytic structure 10 further includes an additional catalytic material disposed on and/or in the zeolite material 12. The additional catalytic material may be capable of catalyzing the formation of methanol from one or both of carbon monoxide (CO) and carbon dioxide (CO$_2$) in the presence of hydrogen. For example, the catalytic structure 10 may include a first catalytic material 20 and a second catalytic material 22 disposed on interior and/or exterior surfaces of the zeolite material 12. As shown in FIG. 3, the first catalytic material 20 and the second catalytic material 22 may be disposed within mesopores 14 of the zeolite material 12. It is contemplated that the first catalytic material 20, the second catalytic material 22, or both the first catalytic material 20 and the second catalytic material 22 also may be disposed within micropores 18 (FIG. 2) of the zeolite material 12.

In some embodiments, the first catalytic material 20 may form a coating extending over surfaces of the zeolite material 12 within the mesopores 14. In additional embodiments, the first catalytic material 20 may be configured as a plurality of nanoparticles disposed within the mesopores 14 of the zeolite material 12. Such nanoparticles may have an average diameter of, for example, less than about 500 angstroms (50 nanometers), and, more particularly, less than about 200 angstroms (20 nanometers). Similarly, the second catalytic material 22 may form a coating extending over surfaces of the zeolite material 12 within the mesopores 14. In additional embodiments, the second catalytic material 22 may be configured as a plurality of nanoparticles disposed within mesopores 14 of the zeolite material 12. Such nanoparticles may have an average diameter of, for example, less than about 500 angstroms (50 nanometers), and, more particularly, less than about 200 angstroms (20 nanometers).

In yet additional embodiments, the first catalytic material 20 and the second catalytic material 22 each may comprise regions of a single layer or coating extending over surfaces of the zeolite material 12 within the mesopores 14.

In some embodiments of the present invention, one or both of the first catalytic material 20 and the second catalytic material 22 may be chemically bound to the zeolite material 12 by, for example, a chemical complex or a chemical bond. In additional embodiments, the first catalytic material 20 and the second catalytic material 22 may be physically bound to the zeolite material 12 by mechanical interference between surfaces of the zeolite material 12 and conformal layers of one or both of the first catalytic material 20 and the second catalytic material 22 formed over such surfaces of the zeolite material 12. In yet other embodiments, there may be substantially no chemical or physical bond between the zeolite material 12 and one or both of the first catalytic material 20 and the second catalytic material 22. For example, nanoparticles of one or both of the first catalytic material 20 and the second catalytic material 22 may be generally loosely disposed within the mesopores 14 of the zeolite material 12.

As previously mentioned, the first catalytic material 20 and the second catalytic material 22 may be capable of catalyzing the formation of methanol from at least one of carbon monoxide and carbon dioxide in the presence of hydrogen. By way of example and not limitation, the first catalytic material 20 may include a metallic material such as, for example, copper, magnesium, zinc, cobalt, iron, nickel, ruthenium, platinum, palladium, or cesium (including alloys based on one or more of such metallic materials). By way of example and not limitation, the second catalytic material 22 may include a metal oxide material such as, for example, zinc oxide, magnesium oxide, zirconium oxide, iron oxide, or tungsten oxide.

One example of a method that may be used to form catalytic structures that embody teachings of the present invention, such as, for example, the catalytic structure 10 shown in FIGS. 1 through 3, will now be described with reference to FIGS. 4 through 7.

Figure 4:
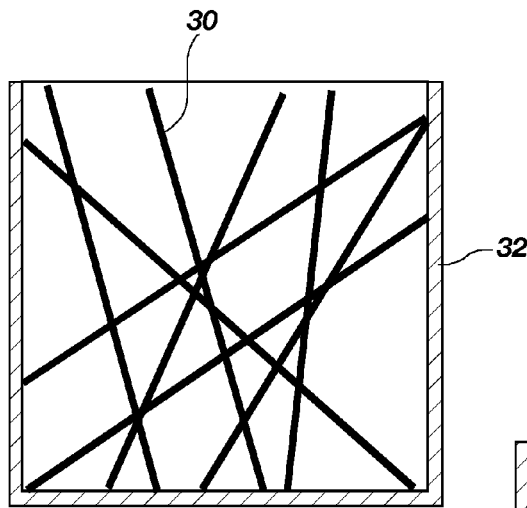
FIGS. 4 through 7 illustrate one example of a method that may be used to fabricate a catalytic structure according to teachings of the present invention.

Referring to FIG. 4, a plurality of template structures 30 may be provided within a container 32. The template structures 30 may have a selected size and shape corresponding to a desired size and shape of pores, such as, for example, the mesopores 14 (FIG. 1), to be formed in the catalytic structure 10. By way of example and not limitation, the template structures 30 may comprise nanoparticles, nanowires, or nanotubes. The template structures 30 may be formed from or include any material that may be subsequently removed from a zeolite material 12 formed around the template structures 30 without significantly damaging or otherwise affecting the zeolite material 12. By way of example and not limitation, the template structures 30 may include carbon. In the embodiment shown in FIG. 4, the template structures 30 include carbon nanowires. Each carbon nanowire may be generally cylindrical and may have an average cross-sectional diameter between about 10 angstroms (1 nanometer) and about 2,000 angstroms (200 nanometers).

In additional embodiments, the template structures 30 may include carbon nanoparticles, carbon nanotubes, or a mixture of at least two of carbon nanowires, nanoparticles, and nanotubes. Furthermore, the template structures 30 optionally may be formed from or include materials other than carbon such as, for example, any polymer material allowing the formation of a zeolite material 12 around the template structures 30 and subsequent removal of the polymer material from the zeolite material 12 without significantly damaging or otherwise affecting the zeolite material 12.

Figure 5:
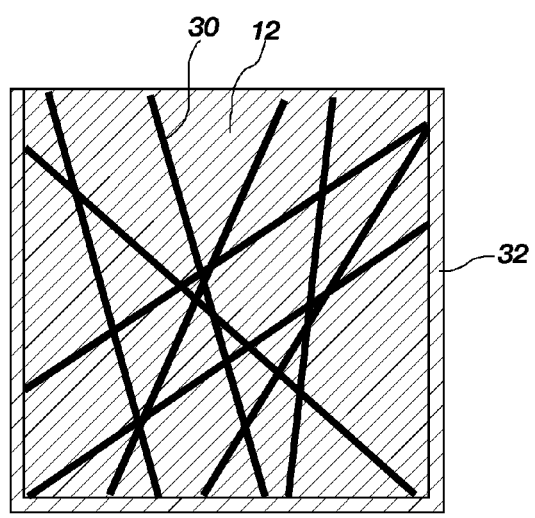

Referring to FIG. 5, a zeolite material 12 may be formed around the template structures 30 using methods known in the art, such as, for example, those methods described in U.S. Pat. No. 3,702,886 to Argauer et al., the entire disclosure of which is incorporated herein in its entirety by this reference.

Figure 6:
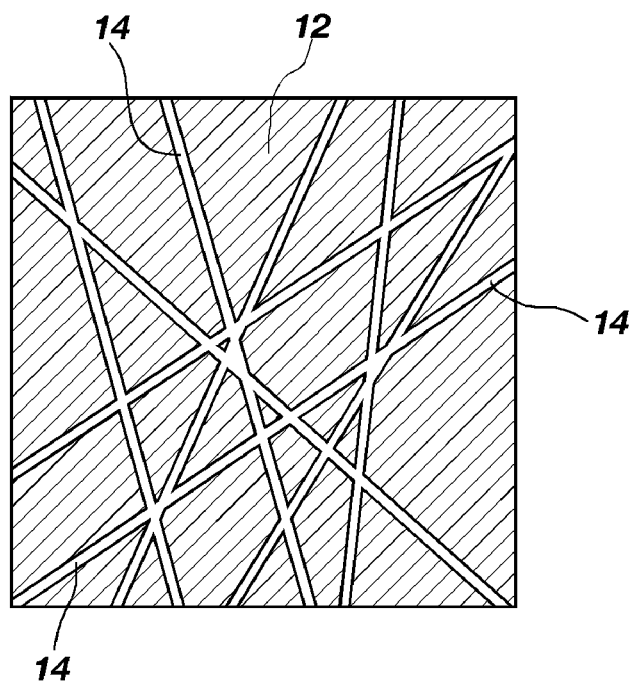

After forming the zeolite material 12 around the template structures 30, the template structures 30 may be removed from within the zeolite material 12 to form mesopores 14 (and optionally macropores), as shown in FIG. 6. If the template structures 30 comprise carbon material, the carbon material may be removed by, for example, calcining in air. By way of example and not limitation, the zeolite material 12 and the template structures 30 may be heated in air to temperatures of about 600° C. for about 20 hours to calcine the carbon material.

After removing the template structures 30 from within the zeolite material 12 to form the mesopores 14 (and optionally macropores), the first catalytic material 20 and the second catalytic material 22 may be provided on and/or in the zeolite material 12.

By way of example and not limitation, particles of the first catalytic material 20 and particles of the second catalytic material 22 (or precursor materials from which the first catalytic material 20 and the second catalytic material 22 can be subsequently formed) may be suspended in a liquid. The liquid and the particles of the first catalytic material 20 and the second catalytic material 22 may be provided within the mesopores 14 of the zeolite material 12 by, for example, immersing the zeolite material 12 in the liquid suspension. The zeolite material 12 then may be removed from the liquid suspension and allowed to dry (at ambient or elevated temperatures) to remove the liquid from the liquid suspension, leaving behind the particles of the first catalytic material 20 and the second catalytic material 22 within the mesopores 14 of the zeolite material 12.

As another example, the first catalytic material 20 and the second catalytic material 22 may be provided on and/or in the zeolite material 12 by precipitation of their respective metal salts (i.e., nitrates or acetates). The precursor salts may be provided in the mesopores 14 of the zeolite material 12 using, for example, the incipient wetness technique. The precursor salts then may be precipitated using standard reagents such as, for example, ammonia or sodium hydroxide. As previously discussed herein, in one embodiment of the present invention, the first catalytic material 20 may include copper and the second catalytic material 22 may include zinc oxide. One method by which copper and zinc oxide may be provided within mesopores 14 of the zeolite material 12 is to immerse the zeolite material 12 in a nitrate solution comprising copper nitrate ($Cu(NO_3)_2$) and zinc nitrate ($Zn(NO_3)_2$). In additional embodiments, the zeolite material 12 may be first immersed in one of a copper nitrate solution and a zinc nitrate solution, and subsequently immersed in the other of the copper nitrate solution and the zinc nitrate solution. Furthermore, the zeolite material 12 may be dried after immersion in the first nitrate solution and prior to immersion in the second nitrate solution.

The copper nitrate and zinc nitrate on and within the zeolite material 12 then may converted to copper oxide (CuO) and zinc oxide (ZnO) by, for example, heating the zeolite material 12 in air to temperatures between about 100° C. and about 250° C. The copper oxide (CuO) then may be converted to copper (Cu) by, for example, flowing hydrogen gas ($H_2$) over the zeolite material 12 at elevated temperatures (for example, about 240° C.).

As yet another example, the first catalytic material 20 and the second catalytic material 22 may be provided on and/or in the zeolite material 12 by preparing a first aqueous solution of zinc nitrate and copper nitrate and adding the zeolite material 12 to the aqueous solution. An additional solution may be prepared that includes hexamethylenetetramine and sodium citrate. This additional solution may be added to the first aqueous solution, and the mixture may be heated in a closed vessel, such as, for example, a Parr acid digestion bomb, to between about 95° C. and about 120° C. for between about one hour and about four hours. The sample then may be filtered, washed, and dried. The sample then may be oxidized in air at temperatures between about 100° C. and about 250° C. to form the copper oxide and zinc oxide, after which the copper oxide may be converted to copper as described above.

In an additional method that embodies teachings of the present invention, the template structures 30 shown in FIG. 4 may include carbon nanotubes. The carbon nanotubes may be impregnated with a solution comprising copper nitrate and zinc nitrate. After forming the zeolite material 12 around the impregnated carbon nanotubes, the carbon nanotubes may be removed by calcining in air, as previously described, and copper and zinc oxide may be formed from the copper nitrate and the zinc nitrate, respectively, as the carbon nanotubes are calcined in the air.

Figure 7:
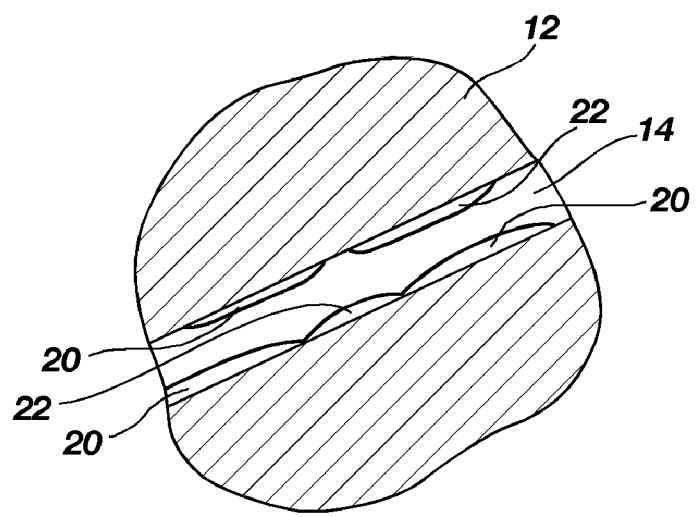

Referring to FIG. 7, the above described method may be used to provide the first catalytic material 20, which may include copper (Cu), and the second catalytic material 22, which may include zinc oxide (ZnO), within mesopores 14 of the zeolite material 12 (and optionally within micropores 18 (FIG. 2) and/or macropores of the zeolite material 12) and to form the catalytic structure 10.

Figure 8:
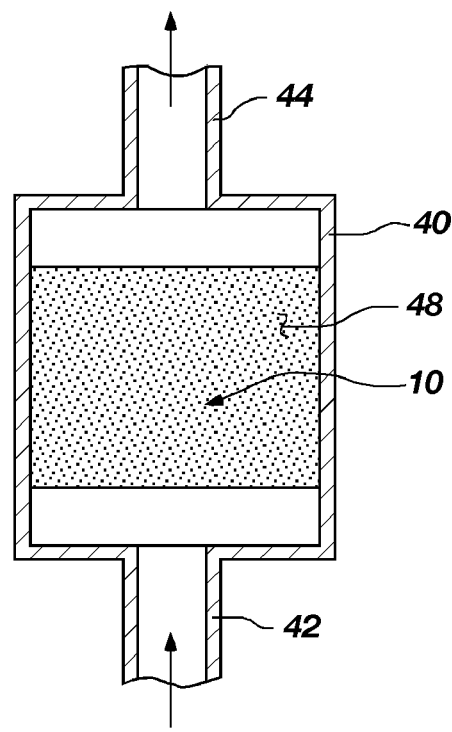
FIG. 8 is a partial cross-sectional view of a reactor that includes a catalytic structure that embodies teachings of the present invention.

Referring to FIG. 8, in some embodiments of the present invention, the catalytic structure 10 may include a quantity of powder 48 comprising relatively fine particles. The particles of the powder 48 may include first and second catalytic materials 20, 22 disposed within a zeolite material 12, as previously described in relation to FIGS. 1 through 3. The powder 48 may be provided within a container 40 having an inlet 42 and an outlet 44, and the powder 48 may be disposed between the inlet 42 and the outlet 44. In this configuration, a gas comprising hydrogen and at least one of carbon monoxide (CO) and carbon dioxide ($CO_2$) may be introduced into the container 40 through the inlet 42. As the gas contacts the powder 48, the powder 48 may catalyze the formation of hydrocarbon molecules having two or more carbon atoms from the carbon monoxide (CO) and carbon dioxide ($CO_2$). In particular, the first catalytic material 20 and the second catalytic material 22 (FIG. 3) may catalyze the formation of methanol from the carbon monoxide (CO) and carbon dioxide ($CO_2$), and the zeolite material 12 may catalyze the formation of hydrocarbon molecules having two or more carbon atoms from the methanol. The hydrocarbon molecules may be collected from the outlet 44 of the container 40 and purified and/or concentrated as necessary or desired.

Figure 9:
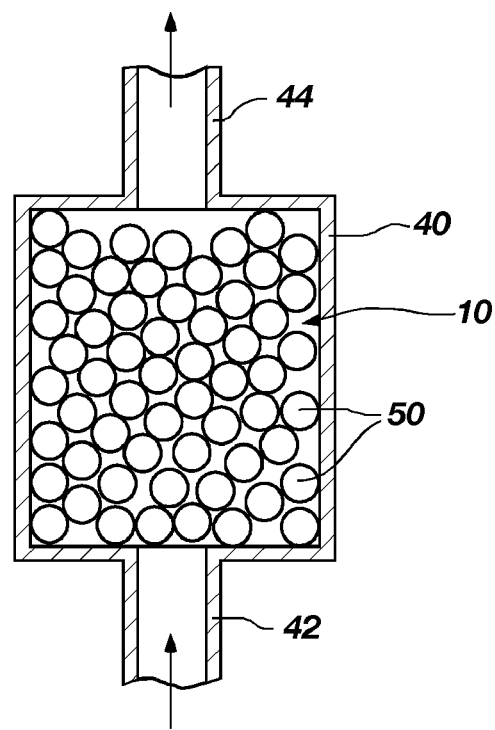
FIG. 9 is a partial cross-sectional view of a reactor that includes another catalytic structure that embodies teachings of the present invention.

Referring to FIG. 9, in additional embodiments of the present invention, the catalytic structure 10 may include a plurality of particles, briquettes, or pellets 50, each of which includes first and second catalytic materials 20, 22 disposed within a zeolite material 12, as previously described in relation to FIGS. 1 through 3. By way of example and not limitation, the pellets 50 may be formed by pressing the powder 48, previously described in relation to FIG. 8, in a die or mold to form the pellets 50. The plurality of pellets 50 may be provided within a container 40, as shown in FIG. 9. In this configuration, a gas comprising at least one of carbon monoxide (CO) and carbon dioxide ($CO_2$) may be introduced into the container 40 through the inlet 42, and the pellets 50 may catalyze the formation of hydrocarbon molecules having two or more carbon atoms from hydrogen and the carbon monoxide (CO) and/or carbon dioxide ($CO_2$), as previously described in relation to FIG. 8.

Figure 10:
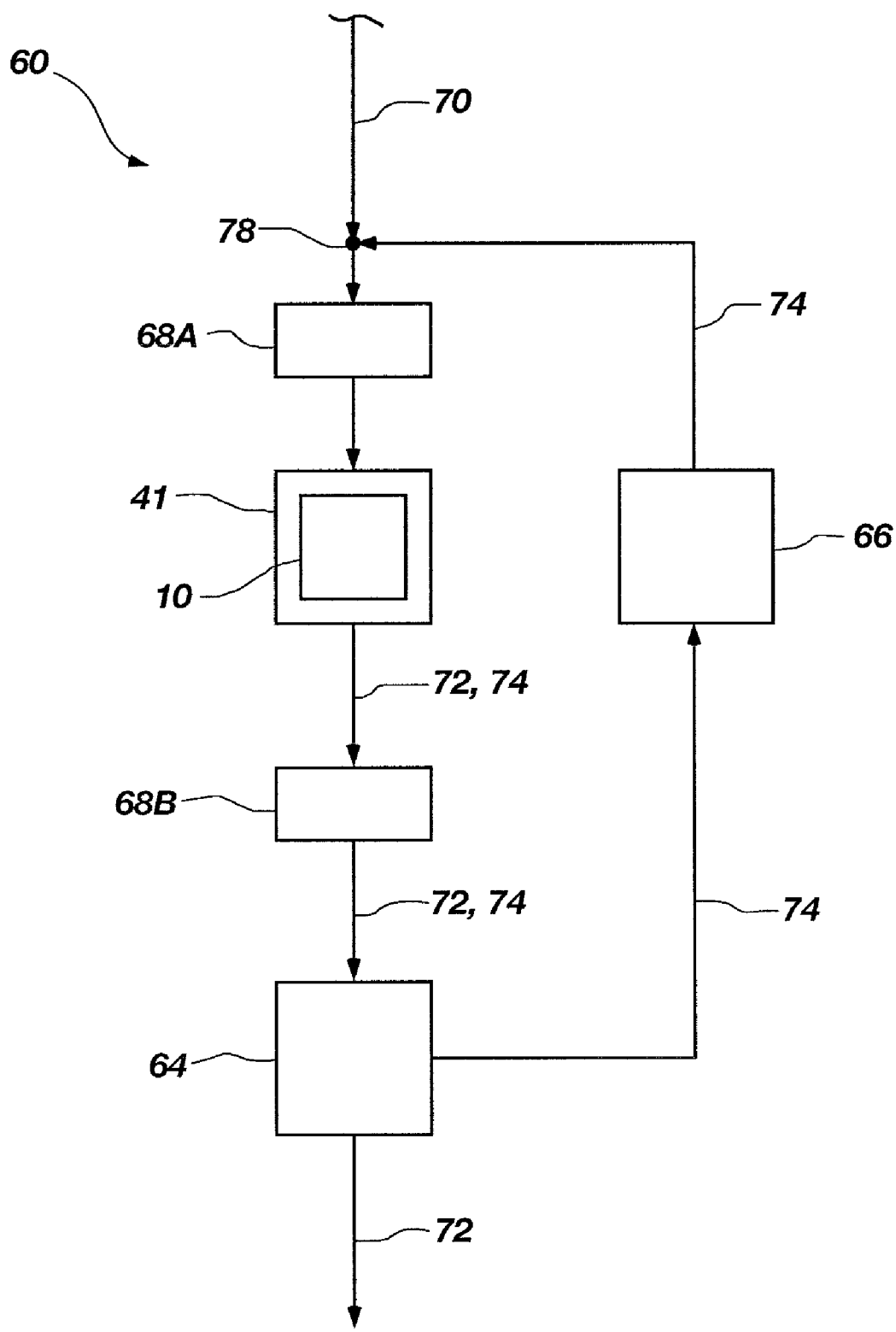
FIG. 10 is a schematic diagram of a system that embodies teachings of the present invention and includes a catalytic structure for catalyzing the formation of hydrocarbon molecules from hydrogen and at least one of carbon monoxide and carbon dioxide.

FIG. 10 is a simplified schematic of a system 60 that embodies teachings of the present invention and that may be used to form hydrocarbon molecules having two or more carbon atoms from carbon monoxide (CO) and/or carbon dioxide ($CO_2$) in the presence of hydrogen using a catalytic structure that embodies teachings of the present invention, such as, for example, the catalytic structure 10 previously described in relation to FIGS. 1 through 3. By way of example and not limitation, the system 60 may include a reactor 41, a gas-liquid separator 64, and a compressor 66. As previously discussed, the reactor 41 may include a catalytic structure that embodies teachings of the present invention, such as, for example, the catalytic structure 10. The system 60 may further include a first heat exchanger 68A for heating a reactant mixture fed to the reactor 41, and a second heat exchanger 68B for cooling products (and any unreacted reactants and/or reaction byproducts) as they exit the reactor 41.

The system 60 may further include a heating device (not shown) for heating the reactor 41 and the catalytic structure 10 to elevated temperatures. For example, a heating device may be configured to heat the reactor 41 and the catalytic structure 10 to a temperature between about 200° C. and about 500° C. Furthermore, the reactor 41 may be pressurized to between about 0.5 megapascals (5 atmospheres) and about 10 megapascals (100 atmospheres).

As shown in FIG. 10, a reactant mixture 70 that includes hydrogen gas and at least one of carbon monoxide (CO) and carbon dioxide ($CO_2$) may be passed through the first heat exchanger 68A and fed to the reactor 41. As previously discussed, the catalytic structure 10 may catalyze the formation of hydrocarbon molecules having two or more carbon atoms from the hydrogen and carbon monoxide (CO) and/or carbon dioxide ($CO_2$). A product mixture 72 (which may include such hydrocarbon molecules), together with any unreacted reactant gasses 74 and reaction byproducts, may be collected from the reactor 41 and passed through the second heat exchanger 68B to the gas-liquid separator 64. The gas liquid separator 64 may be used to separate liquid hydrocarbon products of the product mixture 72 from the unreacted reactant gases 74. The unreacted reactant gasses 74 may be re-pressurized as necessary using the compressor 66 and recombined with the reactant mixture 70 through a three-way valve 78, as shown in FIG. 10.

The liquid hydrocarbon products in the product mixture 72 collected from the gas-liquid separator 64 may then be further processed as necessary or desired. For example, additional distillation equipment (not shown) may be used to purify and concentrate the various hydrocarbon components in the product mixture 72, as necessary or desired.

The catalytic structures, systems, and methods described herein may be used to catalyze the conversion of hydrogen and at least one of carbon monoxide and carbon dioxide to hydrocarbons having two or more carbon atoms with improved catalytic activity and selectivity relative to known catalytic structures, systems, and methods. Furthermore, the catalytic structures, systems, and methods described herein may facilitate economic utilization of carbon dioxide from stationary carbon dioxide sources, such as coal-powered and hydrocarbon-powered electricity generation plants, which otherwise may be vented to atmosphere. Furthermore, the methods described herein may be used to fabricate various catalytic structures, other than those described herein, that include a bi-modal (microporous and mesoporous) or multi-modal (microporous, mesoporous, and macroporous) zeolite material and a metal and/or metal oxide catalyst material disposed on and/or in the zeolite material. Such catalytic structures may be bi-functional. In other words, the zeolite material itself may function as one catalytic material, while the catalytic material disposed on and/or in the zeolite material may function as a second catalytic material. In addition to the synthesis of hydrocarbon molecules from hydrogen and carbon monoxide and/or carbon dioxide, such bi-functional catalytic structures may be useful in many additional applications where it is necessary or desirable to provide different catalytic functions to a single catalytic structure or material.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of synthesizing hydrocarbon molecules having two or more carbon atoms, the method comprising:
   contacting hydrogen and at least one of carbon monoxide and carbon dioxide with a catalytic structure at a temperature greater than about 200° C. and a pressure greater than about 0.5 megapascals, the catalytic structure comprising:
   a zeolite material comprising:
      a first plurality of pores substantially defined by interstitial spaces within a crystal structure of the zeolite material, the first plurality of pores comprising a plurality of micropores; and
      a second plurality of pores dispersed throughout the zeolite material, the second plurality of pores comprising a plurality of mesopores; and
   at least one catalytic material differing from the zeolite material disposed within pores of at least one of the first plurality of pores and the second plurality of pores, the at least one catalytic material comprising a plurality of particles of the catalytic material having an average particle size of less than about 500 angstroms;
   catalyzing the formation of methanol from at least one of carbon monoxide and carbon dioxide in the presence of hydrogen within at least one of the first plurality of pores and the second plurality of pores using the at least one catalytic material; and
   catalyzing the formation of hydrocarbon molecules having two or more carbon atoms from methanol within at least one of the first plurality of pores and the second plurality of pores using the zeolite material.

2. The method of claim 1, wherein contacting at least one of carbon monoxide and carbon dioxide with a catalytic structure comprises supplying a mixture of hydrogen and at least one of carbon monoxide and carbon dioxide to a reactor containing the catalytic structure.

3. The method of claim 1, further comprising:
   removing reaction products and unreacted reactants from the reactor;
   cooling the reaction products and unreacted reactants; and
   separating unreacted reactants from the reaction products, the reaction products comprising hydrocarbon molecules having two or more carbon atoms.

4. The method of claim 2, further comprising recombining the separated unreacted reactants with the mixture supplied to the reactor.

5. The method of claim 1, wherein contacting hydrogen and at least one of carbon monoxide and carbon dioxide with a catalytic structure comprises contacting hydrogen and at least one of carbon monoxide and carbon dioxide with a plurality of pellets each comprising the zeolite material and the at least one catalytic material.

6. The method of claim 1, further comprising selecting the plurality of particles of the catalytic material to comprise a plurality of metallic particles.

7. The method of claim 6, further comprising selecting each metallic particle of the plurality of metallic particles to comprise at least one of copper, magnesium, zinc, cobalt, iron, nickel, ruthenium, platinum, palladium, and cesium.

8. The method of claim 6, further comprising selecting the plurality of particles of the catalytic material to comprise a plurality of metal oxide particles.

9. The method of claim 8, further comprising selecting each metal oxide particle of the plurality of metal oxide particles to comprise at least one of zinc oxide, magnesium oxide, zirconium oxide, iron oxide, and tungsten oxide.

10. The method of claim 1, further comprising selecting the at least one catalytic material to comprise copper and zinc oxide.

11. The method of claim 1, further comprising forming the second plurality of pores to comprise a plurality of elongated channels.

12. The method of claim 11, further comprising forming each elongated channel of the plurality of elongated channels to be generally cylindrical and have an average diameter in a range extending from about 20 angstroms to about 500 angstroms.

13. The method of claim 11, further comprising forming the second plurality of pores to comprise a plurality of generally spherical pores.

14. The method of claim 1, further comprising selecting the zeolite material to comprise a framework type selected from MFI, BEA, FAU, MOR, FER, ERI, OFF, CHA and AEI.

15. The method of claim 14, further comprising selecting the zeolite material to comprise an aluminosilicate-based material, an aluminophosphate-based material, or a silicoaluminophosphate-based material.

16. The method of claim 15, further comprising selecting the zeolite material to comprise ZSM-5.

\* \* \* \* \*